(12) United States Patent
Levine et al.

(10) Patent No.: US 8,329,941 B2
(45) Date of Patent: Dec. 11, 2012

(54) PROCESS FOR THE EXTRACTION OF HIGH MOLECULAR WEIGHT NAPHTHENIC ACIDS FROM CALCIUM NAPHTHENATE SALTS

(75) Inventors: Steven W. Levine, Flemington, NJ (US); Manuel A. Francisco, Phillipsburg, NJ (US); Sharon A. Feiller, Allentown, PA (US); Clifford C. Walters, Milford, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 282 days.

(21) Appl. No.: 12/631,177

(22) Filed: Dec. 4, 2009

(65) Prior Publication Data

US 2010/0160680 A1   Jun. 24, 2010

Related U.S. Application Data

(60) Provisional application No. 61/193,791, filed on Dec. 23, 2008.

(51) Int. Cl.
*C07C 61/00* (2006.01)
(52) U.S. Cl. ........................................ 562/511
(58) Field of Classification Search .................. None
See application file for complete search history.

(56) References Cited

U.S. PATENT DOCUMENTS 6,096,196 A * 8/2000 Varadaraj et al. ............. 208/263

* cited by examiner

*Primary Examiner* — Sudhakar Katakam
(74) *Attorney, Agent, or Firm* — Glenn T. Barrett; Malcolm D. Keen

(57) ABSTRACT

A method for recovering high molecular weight naphthenic tetra-acids, particularly ARN acids from a calcium naphthenate deposit. Calcium naphthenate deposits contain large amounts of calcium naphthenate salts of ARN acids. The method dual solvent extraction process in which the naphthenic tetra-acids chemically bound as calcium naphthenate salts are converted into free acid monomers by an aqueous acid. The resulting free acid monomers are then dissolved into an organic solvent phase and the counterions dissolve in the aqueous acid phase. The naphthenic tetra-acids are then recovered from the organic solvent phase.

14 Claims, 3 Drawing Sheets

PROCESS FOR THE EXTRACTION OF HIGH MOLECULAR WEIGHT NAPHTHENIC ACIDS FROM CALCIUM NAPHTHENATE SALTS

CROSS REFERENCE TO RELATED APPLICATION

This application relates to and claims priority to U.S. Provisional Patent Application No. 61/193,791, filed on Dec. 23, 2008.

FIELD

The disclosed subject matter relates to a process for the extraction of high molecular weight naphthenic tetra-acids from calcium naphthenate salts.

BACKGROUND

Naphthenic acids are carboxylic acids that occur in most crude oils as trace components and in some, biodegraded oils in significantly greater concentrations. Total acids in crude oils is commonly semi-quantified by titration with KOH and expressed in terms of total acid number (TAN). Conventional TAN measurements are not precisely a measure of total acids in a crude oil, but a measure of the amount of KOH needed to achieve the deflection (neutralization) point. Accordingly, TAN is an approximation of the amount of naphthenic acids. The acidity of high TAN oils may cause emulsion and corrosion problems in both production and refining. Solid deposits, recently identified as calcium naphthenates, can result in substantial damage and lose of production.

Under certain conditions, the naphthenic acids present in acidic crude oil will precipitate with $Ca^{2+}$ ions that are present in the co-produced water to form calcium naphthenate solids. Other cations are involved to a lesser extent forming a variety of metal naphthenates (e.g., ferrous iron and magnesium). This solid precipitation accumulates predominantly in oil-water separators and desalters, but naphthenates also can deposit in subsea, topside, or surface facilities and pipelines.

A great deal of research has been pursued to characterize the naphthenic acid responsible for the calcium deposits. It has been recently determined that a specific family of high molecular weight tetracarboxylic acids, termed ARN Acids, appears to be the major constituent responsible for the calcium naphthenate deposits (ARN is not an acronym, but is Old Norwegian for "eagle"). ARN acids are high molecular weight molecules with four carboxylic acid groups, each at the end of a long aliphatic chain, forming a four-fingered molecule with polar tips. The ARN acids are a specific family of $\sim C_{80}$ tetracarboxylic acids. A majority of the ARN acids have a molecular weight ranging from about 1228 to about 1236 atomic mass units (amu) with one of the main acids having a molecular weight of 1232 amu and a molecular formula of $C_{80}H_{142}O_8$. The ARN acids do not have an aromatic or alkenes function present and quaternary carbons do not exist. The ARN acids can have 4-8 sites of unsaturation (or 4-8 cyclopentyl rings) and are believed to be derived from archaeal $C_{80}$ lipids.

The proposed structure of the major ARN acid is 6:17,10:18,10':18',6":17",10":18",10'":18'")-hexacyclo-20-bis-16,16"-biphytane-1,1',1",1'"-tetracarboxylic acid. The molecule contains two biphytanyl diacids, each with three pentacyclic rings joined together by a linkage at the $C_{20}$ methyl groups, as described in Lutnaes B. F., Brandal Ø., Sjöblom J., and Krane J. (2006) Archaeal $C_{80}$ isoprenoid tetraacids responsible for naphthenate deposition in crude oil processing. *Organic & Biomolecular Chemistry* 4, 616-620, incorporated by reference in its entirety herein.

The structure of a representative archaeal $C_{80}$ isoprenoid tetra-acid is:

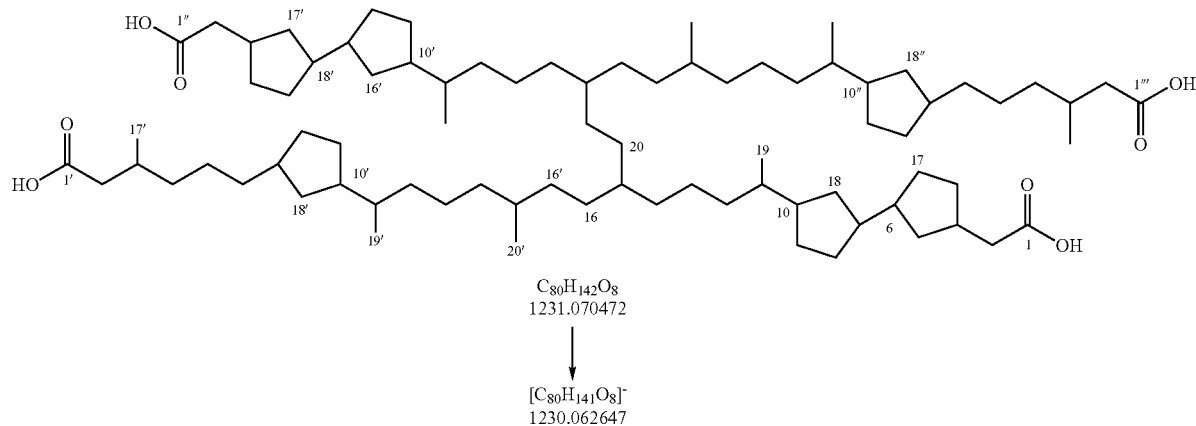

The four carboxylic acid groups afford the molecule unusually high reactivity. These four carboxylic groups tend to create polymeric salt when coordinated with divalent metal ions. This woven polymeric-like structure yields a very sticky deposit that hardens upon contact with air.

A method for selectively isolating carboxylic acids from oils and calcium naphthenates using an Acid-Ion Exchange Resin procedure has been described in Mediaas et al. (2003) The Acid IER Method—a Method for Selective Isolation of Carboxylic Acids from Crude Oils and Other Organic Solvents, Society of Petroleum Engineers Paper 80404. The ion-exchange method is suitable when dealing with cleaning up Ca-naphthenate precipitates as most of the material is composed of ARNs. However, this method is likely not suitable for industrial scale separation because the resins will eventually foul with the associated hydrocarbons/aspahltenes. Furthermore, the use of ion-exchange resins on an industrial scale level may be cost prohibitive.

A need therefore exists for alternative and more efficient and effective methods to isolate and extract high molecular weight naphthenic tetra-acids from calcium naphthenate salts.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with one aspect of the disclosed subject matter, as embodied and broadly described, a method is provided for recovering high molecular weight naphthenic tetra-acids, particularly ARN acids, from a calcium naphthenate deposit. The naphthenic tetra-acid recovered from such a method also is disclosed herein. Calcium naphthenate deposits contain large amounts of calcium naphthenate salts of ARN acids. The disclosed subject matter outlines a process to isolate the ARN tetra-acids from the calcium naphthenate deposits that have been recovered during upstream production of crude oils. The method includes a dual solvent extraction process in which the naphthenic tetra-acids chemically bound as calcium naphthenate salts are converted into free acid monomers by an aqueous acid. The resulting free acid monomers are then dissolved into an organic solvent phase and the counterions dissolve in the aqueous acid phase. The naphthenic tetra-acids are then recovered from the organic solvent phase.

The method includes the steps of providing calcium naphthenate deposits, the deposits including calcium naphthenate salts of naphthenic tetra-acids and entrained crude oil, and providing an aqueous solvent solution comprising an aqueous acid and an organic solvent, the aqueous acid and the organic solvent present in a volumetric ratio effective to dissociate the naphthenic tetra-acids and calcium salt and allow the tetra-acids to dissolve in the organic solvent. Preferably, the calcium naphthenate deposit is finely ground to a powder. The method further includes adding the calcium naphthenate deposit to the aqueous solvent solution in an effective mass ratio of aqueous solvent solution to calcium naphthenate deposit to form a multiphase mixture; separating the multiphase mixture into a plurality of phases including an aqueous acids phase and an organic solvent phase; and recovering the naphthenic tetra-acids from the organic solvent phase. Preferably, recovering the naphthenic tetra-acids from the organic solvent phase includes evaporation of the organic solvent. In accordance with one embodiment, the multiphase mixture can be filtered to remove solids.

In accordance with a preferred embodiment, following the initial separation of the aqueous acid phase and the organic solvent phase and prior to the recovery step, the aqueous acid phase is washed with an effective amount of additional organic solvent to dissolve any additional tetra-acids that are present in the aqueous phase into the organic solvent. The aqueous phase and the organic solvent phase are then separated and the organic solvent phase is combined with the organic solvent phase from the previous separation.

In addition, in order to remove any water present in the organic phase prior to the recovery step, the combined organic solvent layers or phases can be dried using a chemical drying agent, which can then be removed by filtration.

In accordance with a preferred embodiment, the aqueous acid is hydrochloric acid and the organic solvent is methylene chloride. In accordance with one embodiment, the drying agent is anhydrous sodium sulfate.

In accordance with one embodiment, the aqueous solvent solution includes a volumetric solution of 1:1 of the aqueous acid to the organic solvent. Preferably, the effective mass ratio of aqueous solvent solution to calcium naphthenate deposit is at least 40:1.

In accordance with another embodiment, the calcium naphthenate deposits occur from the production of a crude oil, wherein the crude oil is a high-neutralization number (HNN) crude oil.

According to another aspect, the disclosed subject matter includes multi-step, dual solvent extraction process in which the naphthenic tetra-acids chemically bound as calcium naphthenate salts are converted into free acid monomers by an aqueous acid. The resulting free acid monomers are then dissolved into an organic solvent phase and the counterions dissolve in the aqueous acid phase. The naphthenic tetra-acids are then recovered from the organic solvent phase.

These and other features of the disclosed subject matter will become apparent from the following detailed description of preferred embodiments which, taken in conjunction with the accompanying drawings, illustrate by way of example the principles of the disclosed subject matter.

BRIEF DESCRIPTION OF THE DRAWINGS

The disclosed subject matter will now be described in conjunction with the accompanying drawings in which.

DETAILED DESCRIPTION

Reference will now be made in detail to the various aspects of the disclosed subject matter. The method and corresponding steps of the disclosed subject matter will be described in conjunction with the figures and examples provided herein.

A method for recovering high molecular weight naphthenic tetra-acids, particularly ARN acids, from a calcium naphthenate deposit is provided. Calcium naphthenate deposits contain large amounts of calcium naphthenate salts of tetra-acids. A process is disclosed to isolate the tetra-acids from the calcium naphthenate deposits, which have been recovered during upstream production of crude oils. The method includes a multi-step, dual solvent extraction process in which the naphthenic tetra-acids chemically bound as calcium naphthenate salts are converted into free acid monomers by an aqueous acid. The resulting free acid monomers are then dissolved into an organic solvent phase and the counterions dissolve in the aqueous acid phase. The naphthenic tetra-acids are then recovered from the organic solvent phase.

Generally, the method includes the steps of providing calcium naphthenate deposits, the deposits including calcium naphthenate salts of naphthenic tetra-acids and entrained crude oil and providing an aqueous solvent solution comprising an aqueous acid and an organic solvent, the aqueous acid and the organic solvent present in a volumetric ratio effective to dissociate the naphthenic tetra-acid and calcium salt and allow the tetra-acid to dissolve in the organic solvent. The method further includes adding the calcium naphthenate deposit to the aqueous solvent solution in an effective mass ratio of aqueous solvent solution to calcium naphthenate deposit to form a multiphase mixture; separating the multiphase mixture into a plurality of phases including an aqueous acids phase and an organic solvent phase; and recovering the naphthenic tetra-acids from the organic solvent phase. Preferably, recovering the naphthenic tetra-acids from the organic solvent phase includes evaporation of the organic solvent. In accordance with one embodiment, the multiphase mixture can be filtered to remove solids.

The extraction process described herein can be conducted as a batch, continuous or semi-continuous system. Preferably, the system should be conducted to maximize intimate contacts between the naphthenates salts-naphthenic acids and the solvent system. Suitable mixing devices would be those typically used for solid-liquid blending, such as mixing tanks, baffle mixers, mixing valves and the like.

Figure 1:
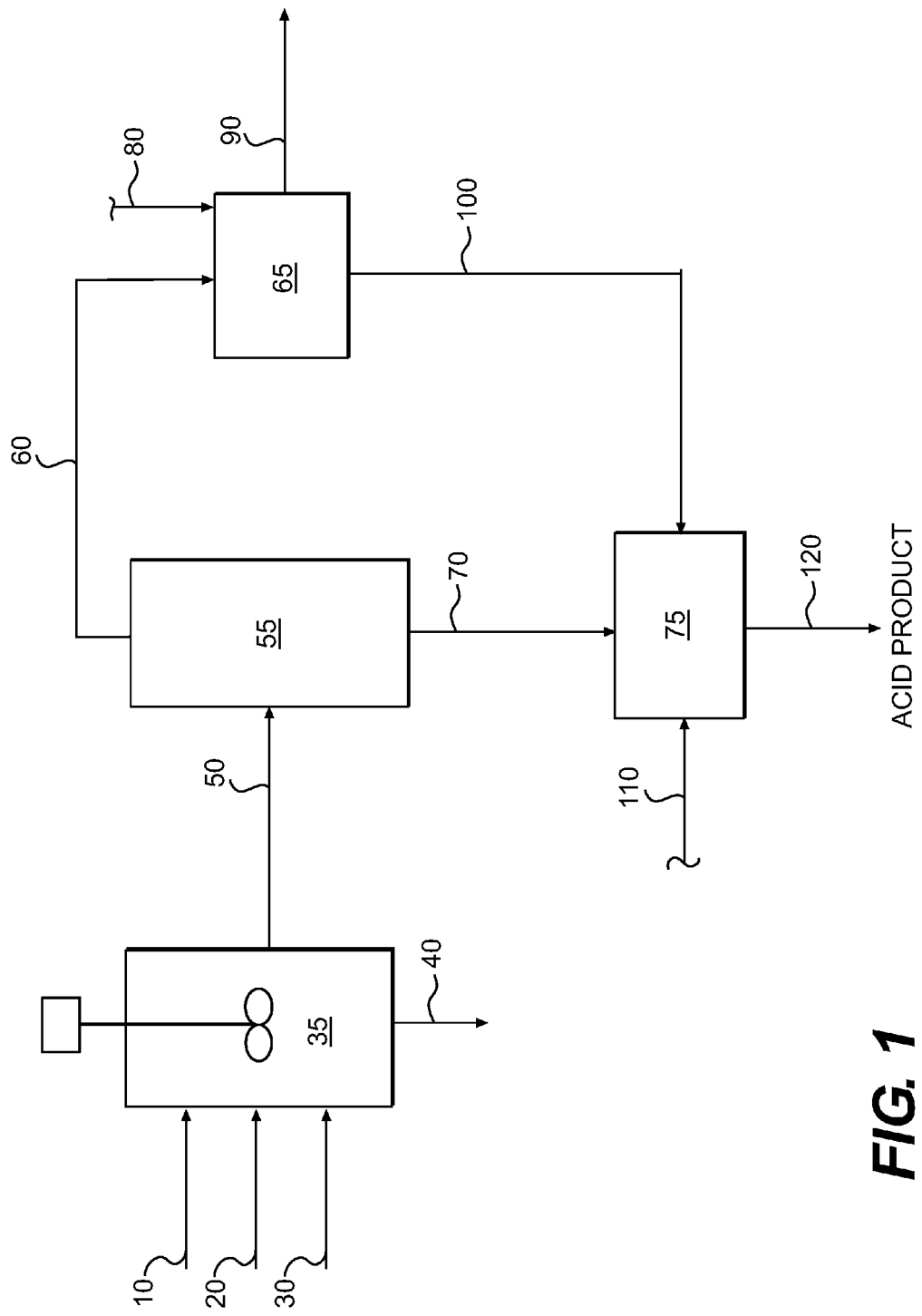
FIG. 1 is a schematic flow diagram depicting one embodiment of the disclosed subject matter.

For purpose of illustration and not limitation the method is depicted schematically in FIG. 1. The method described herein includes a semi-continuous or continuous process embodiment of the disclosed process. The process includes providing calcium naphthenate deposits 10, the deposits comprised of calcium naphthenate salts of naphthenic tetra-acids and entrained crude oil. Preferably, the deposits are finely ground into a powder. The method further includes providing an aqueous solvent solution comprising an aqueous acid 20 and an organic solvent 30. The aqueous acid 20 and the organic solvent 30 are fed to an extraction-mixing device 35, for example, a mixing tank. The aqueous acid and the organic solvent are present in a volumetric ratio in an amount that is effective to dissociate the naphthenic tetra-acid and calcium salt and allow the tetra-acid to dissolve in the organic solvent. Typically, the extraction is conducted using a volume ratio of the aqueous acid solvent to the organic solvent in the range of 1 to 500 parts by volume of aqueous acid solvent per part by volume of organic solvent. However it shall be understood by those skilled in the art that any suitable ratio can be used which is effective is dissociating the tetra-acids and calcium salts and allowing the tetra-acids to dissolve in the organic solvent.

In one embodiment, the solvents 20,30 are initially fed to the mixing device, the device is continuously stirred and after a predetermined time, the deposits 10 are added to the solvent solution as the multiphase mixture continues to be stirred. In an alternative embodiment, the calcium naphthenate deposit 10 is added simultaneously with the solvents 20, 30 to the mixing device 35.

Generally, the extraction is conducted using a weight ratio of total aqueous solvent solution to calcium naphthenate deposits in the range of about from 1 to 500 parts by weight of total solvent solution per part by weight of calcium naphthenate deposits. Typically, the extraction is conducted at temperatures that are solvent specific where the lower temperature is limited by the melting point of the solvent.

Suitable mixing devices 35 which can be used include, for example, mixing tanks, baffle mixers, mixing valves and the like. The length of time that the solvent solution and deposits are mixed generally ranges from 1 minute to 1 day, depending upon the mixing conditions. It shall be understood that optimum mixing or contact times will vary with the efficiency of the particular mixing device used and can be determined by routine procedures. If any solids are present in the mixing tank, the solids are removed as bottoms product 40 from the mixing device. When all of the calcium naphthenates are dissolved in the acid, the solids can include acid insoluble inorganic salts, oxides, and metals.

The aqueous acid and organic extraction solvents are immiscible and, accordingly, can be separated from each other by allowing the mixture to settle into two phases and then separating the two phases by any suitable procedure. The aqueous solvent mixture and dissociated and dissolved deposits 50 can be fed from the mixing device 35 to the phase separation vessel 55, for example a settling tank. The total mixture is then allowed to separate. The separation can be achieved using gravity settling, electrostatic field separation, centrifugation or a combination thereof. The bottoms organic solvent 70, which contains the dissolved tetra-acids is discharged to the final separator 75 and the upper aqueous acid 60 is fed to another separation vessel 65. If any residual sediment is present in the separation vessel 65, the sediment can be removed using conventional filtration techniques and processes.

In separation vessel 65, additional organic solvent 80 is added to upper aqueous acid. The organic solvent is preferably identical to the first organic solvent 30 used in the initial mixing device 35. The dual solvent mixture comprising aqueous acid and organic solvent are allowed to separate and the bottoms organic solvent phase 100 is fed to the final separator 75. The upper aqueous acid 90 is discharged from separation vessel 65 as is or can be subjected to further processing, including, but not limited to recycling.

Although only two separation vessels are depicted in FIG. 1, it shall be understood that any number of additional separation vessels can be used for additional washing of the aqueous acid layer with organic solvent to dissolve further any acids present in the aqueous layer into the organic solvent. The organic solvent phases from any additional separation steps that may be included are all collected and fed to the final vessel 75.

If any water is present, the organic solvent layers can be dried using a suitable chemical drying agent 110. The chemical drying agent is allowed to contact the organic solvent layer for a predetermined time and temperature. The chemical drying agent is then removed, typically by filtration. Suitable chemical drying agents to remove water in the extracted organic phase include, but are not limited to anhydrous sodium sulfate, gypsum (calcium sulfate), calcium chloride, or silica gel.

Following the drying step, the naphthenic tetra-acids products are then recovered from the organic solvent phase. The organic solvent is typically removed by distillation and/or evaporation techniques using conventional devices and processes, including but not limited to rotary evaporation, atmospheric evaporation, centrifugal evaporation, hot plate evaporation under nitrogen-purge, or RapidVap vacuum evaporation systems.

In accordance with the disclosed subject matter, the final material isolated via dual solvent extraction process is the high molecular weight naphthenic tetra-acids, particularly the ARN tetra-acids. The material isolated 120 comprises the naphthenic tetra-acids in addition to a relatively small amount of entrained crude oil. The addition of the isolated naphthenic tetra-acids 120 to crude oil is effective in reducing or preventing fouling in a refinery component, as described in copending U.S. Provisional Patent Application No. 61/193,621 filed on Dec. 11, 2008.

In accordance with yet another embodiment, the entrained crude within the calcium naphthenate deposits can be quantified using a second extraction process on the solid calcium naphthenate deposits. The process (not illustrated) for quantifying the entrained crude includes grinding the deposits to a powder, adding the powdered solids to a Soxhelt thimble and extracting with toluene for approximately 20 hours. The extracts from the toluene, which are the entrained crude, are extracted to dryness and weighed.

In accordance with one embodiment, the aqueous acid includes any compound which can covert the naphthenic acids chemically bound as naphthenate to free acid monomers which dissolve into the organic solvent, leaving the counter ions in the aqueous acid phase. Suitable aqueous acids include, but are not limited to, hydrochloric, sulfuric, nitric, acetic, or phosphoric acid. In a preferred embodiment, the aqueous acid includes hydrochloric acid.

For purpose of illustration and not limitation, the organic solvent includes any suitable compound in which the naphthenic tetra-acids dissolve. Suitable organic solvents include, but are not limited to, alkyl halides, light aromatic hydrocarbons, or light hydrocarbon-light alcohol mixtures. In a preferred embodiment, the organic solvent is methylene chloride.

Figure 2:
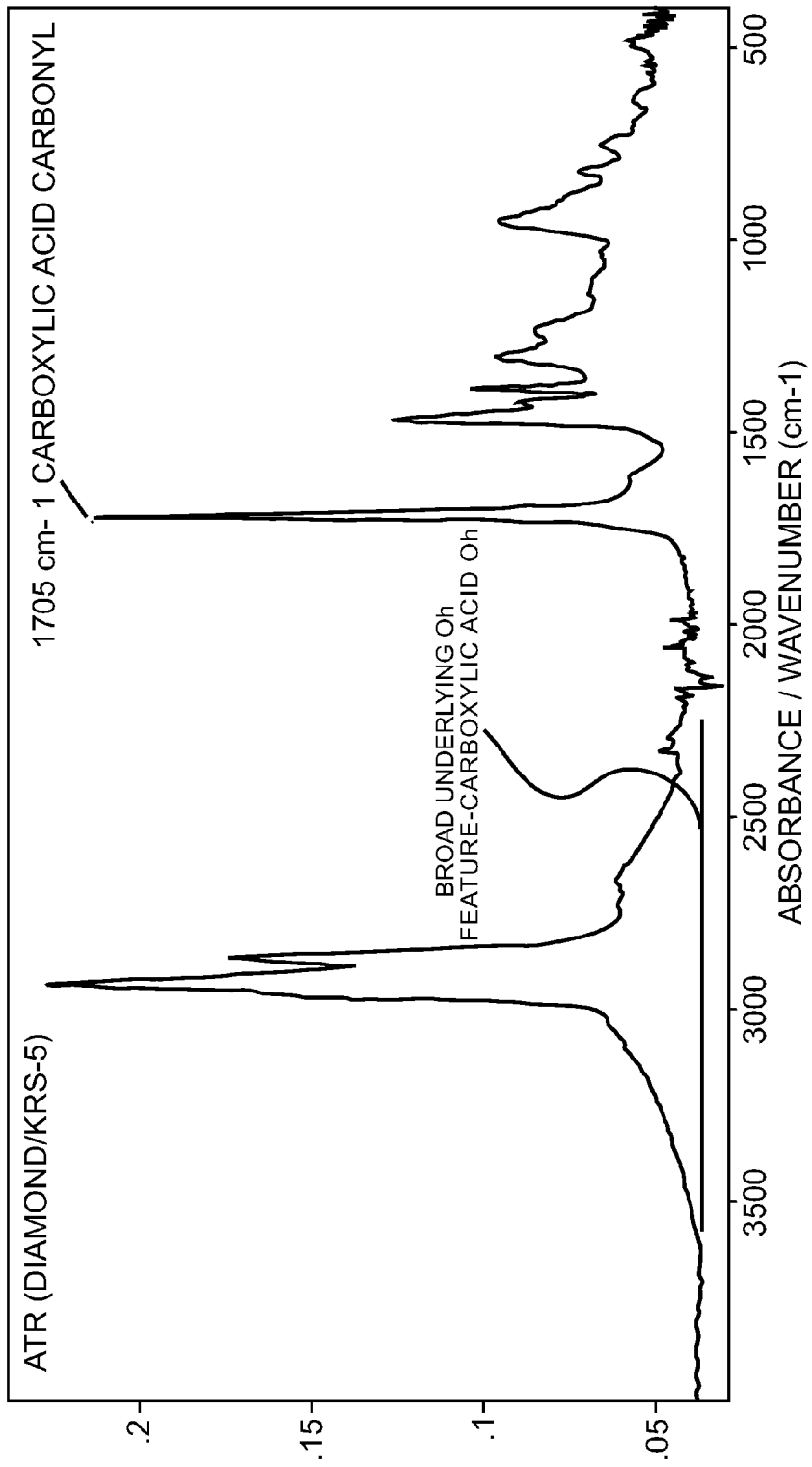
FIG. 2 is a graph illustrating an infrared spectroscopy scan of naphthenic tetra-acids recovered from calcium naphthenate deposits in accordance with the disclosed subject matter.

Generally, the dual solvent extraction process described herein is effective in extracting the high molecular weight naphthenic tetra-acids at purity ranging from about 10% to about 100% with a yield on the deposits ranging from about 10% to about 100%. As illustrated in FIG. 2, for purpose of illustration and not limitation, an infra-red scan of the extracted acid product indicates the presence of carboxylic acids, demonstrating a successful isolation of the ARN tetra-acids in the calcium naphthenate deposits using the process describe herein.

In accordance with one embodiment, the extracted product includes high molecular weight naphthenic tetra-acids, which are molecules having four carboxylic acid groups, each at the end of a long aliphatic chain, forming a four-fingered molecule with polar tips. In accordance with one embodiment, the high molecular weight naphthenic tetra-acid has an atomic molecular weight great than 1230 atomic mass units (amu).

In accordance with a preferred embodiment of the disclosed subject matter, the high molecular weight naphthenic tetra-acids which are extracted from the calcium naphthenate deposits are ARN acids. ARN acids are a specific family of $~C_{80}-C_{81}$ tetracarboxylic acids. A majority of the ARN acids have a molecular weight ranging from about 1228 to about 1236 atomic mass units (amu) with one of the main acids having a molecular weight of 1232 amu. The ARN acids do not have an aromatic or alkenes function present and quaternary carbons do not exist. The ARN acids can have 4-8 sites of unsaturation (or 4-8 cyclopentyl rings).

In accordance with one embodiment, the ARN acid extracted is the archaeal $C_{80}$ isoprenoid, whose empirical formula is $C_{80}H_{142}O_8$ and whose structure is 6:17,10:18,10':18',6":17",10":18",10'":18")-hexacyclo-20-bis-16,16"-bi-phytane-1,1',1",1'''-tetracarboxylic acid. This $C_{80}$ isoprenoid molecule contains two biphytanyl diacids, each with three pentacyclic rings joined together by a linkage at the $C_{20}$ methyl groups and its structure is represented by:

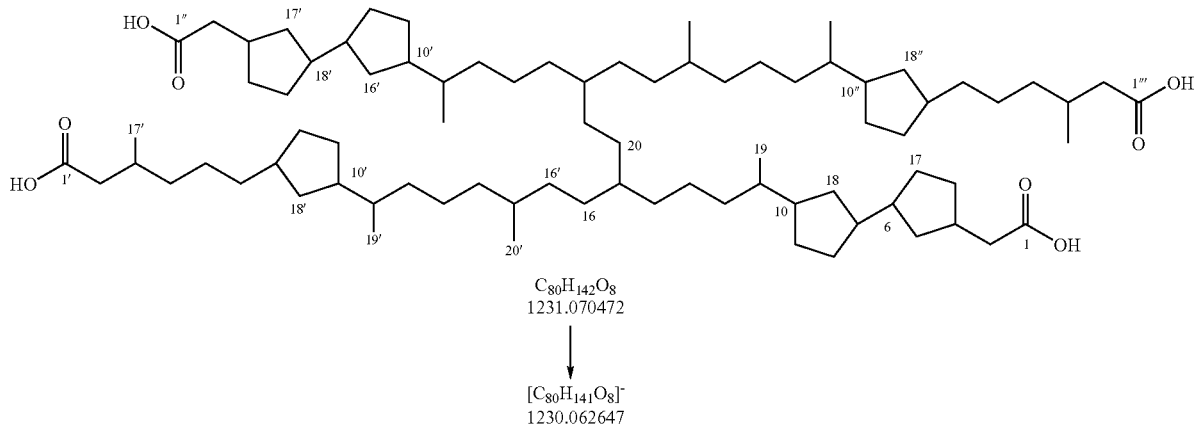

Therefore, in accordance with the disclosed subject matter, the high molecular weight naphthenic tetra-acids are extracted from the calcium naphthenate deposits, the deposits including high molecular weight naphthenic tetra-acid calcium salts. Typically, calcium naphthenate deposits occur during the production of high neutralization number (HNN) crude oils.

While a particular form of the disclosed subject matter has been described, it will be apparent to those skilled in the art that various modifications can be made without departing from the spirit and scope of the disclosed subject matter.

EXAMPLES

The present application is further described by means of the examples, presented below. The use of such examples is illustrative only and in no way limits the scope and meaning of the disclosed subject matter or of any exemplified term.

Example 1

In this example, high molecular weight naphthenic tetra-acids were extracted from solid calcium naphthenate deposits. The extraction process of this example is an example of a batch application of the disclosed process.

Solid calcium naphthenate deposits were finely ground into a powder using a mechanical grinder. An aqueous solvent solution was prepared, the solution including 1M aqueous hydrochloric acid and methylene chloride solvent in a 1:1 ratio by volume. The solution was placed into a mixing device and continuously stirred. The ground deposit was then added to the solvent solution at a 40:1 total solvent solution to solid deposit ratio, and the total mixture of solvent and solids was stirred overnight at room temperature. The total mixture was then filtered and the filtered solids were dried. When all of the calcium naphthenates are dissolved in the acid, the solids can include acid insoluble inorganic salts, oxides, and metals. The solvent solution including aqueous hydrochloric acid and methylene chloride were allowed to separate into a multiphase mixture including the aqueous acid layer, the organic solvent layer and solids. The entire mixture was suction filtered and the filtered solids were dried and weighed. When all of the calcium naphthenates are dissolved in the acid, the solids can include acid insoluble inorganic salts, oxides, and metals. The hydrochloric acid phase and the methylene chloride phase were then separately withdrawn. The aqueous hydrochloric acid phase was washed twice with small amounts of additional methylene chloride solvent and the washes were combined with the extract from the initial methylene chloride phase. The combined methylene chloride layers were then dried over anhydrous sodium sulfate overnight and recovered by filtration. The acid concentrate product was then recovered by evaporation of the methylene chloride solvent and weighed.

The final material isolated was the high molecular weight naphthenic tetra-acids concentrate. This extracted material contains the tetra-acids obtained from the calcium salts in addition to some entrained crude oil. As illustrated in FIG. 1, an infra-red (IR) scan of the ARN concentrate strongly indicates the presence of carboxylic acids, demonstrating a successful isolation (concentration) of the tetra-acids in the upstream deposit. The raw weight measurements from the Experiment are tabulated in Table 1.

TABLE 1

Weight Measurements from Example 1

| | Weight (g) | Experimental |
|---|---|---|
| Starting Weight (g) | 5 | Upstream calcium naphthenate deposits |
| Residual (g) | 1.2 | |
| Extracted Weight (g) | 1.7 | Extraction with Methylene Chloride and 1M HCL |

Example 2

In this example, the entrained crude within the sample was quantified by conducting a second extraction on the solid naphthenate deposits. First, 5 grams of deposits were finely ground into a powder. The powdered solids were added to a Soxhlet cellulose thimble and extract overnight with toluene. The extracted solids were then dried and weighed and any residual toluene was removed by rotary evaporation. The extracted material is the entrained crude. The raw weight measurements from the Experiment are tabulated in Table 2.

TABLE 2

Weight Measurements from Example 2

| | Weight (g) | Experimental |
|---|---|---|
| Starting Weight (g) | 5.00 | |
| Entrained Crude (Soxhlet) (g) | 0.8 | Soxhlet ran for 24 hours with Toluene |

Figure 3:
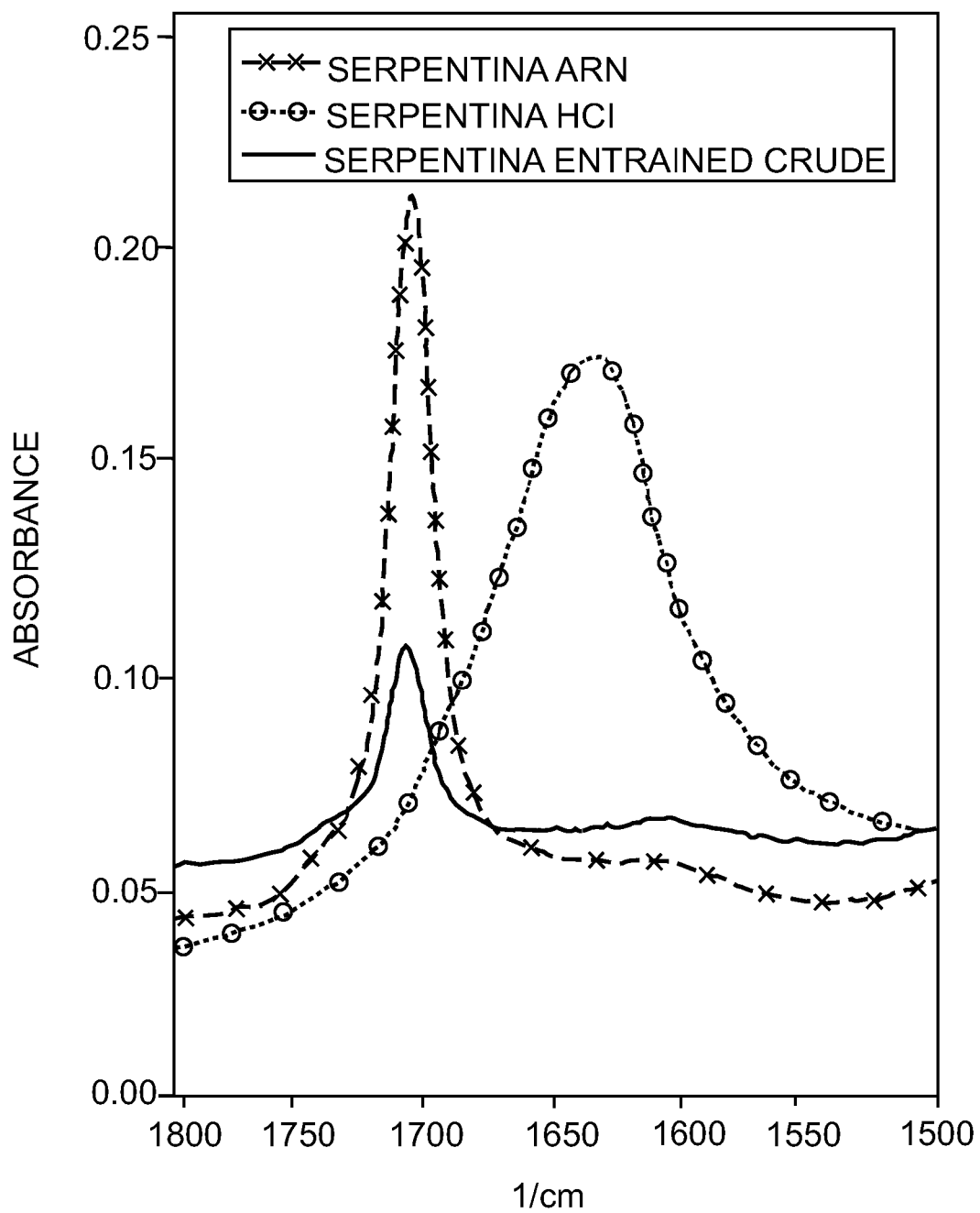
FIG. 3 is a graph illustrating an infrared spectroscopy scan of the carboxylic acid region for the concentrated naphthenic tetra-acids extracted, the entrained crude and the aqueous acid phase from the extraction.

Infra-red (IR) scans were conducted for: i) the extracted high molecular weight naphthenic tetra-acids concentrate, ii) the aqueous hydrochloric acid phase (From Example 1) in addition to iii) the entrained crude. FIG. 3 illustrates the carboxylic acid region of the IR scan. As illustrated in FIG. 3, the entrained crude illustrates some carboxylic acid presence but confirms that the aqueous phase is essentially free of carboxylic acids.

From the two extractions performed in Examples 1 and 2, it is possible to calculate the compositions of both the original deposits and the concentrated ARN extract and the yields. The composition of the solid calcium naphthenate deposits as well as the yields are tabulated in Table 3. In the table, S is solids, A is ARN acids, C is calcium and other aqueous-soluble materials, and E is entrained oil. As illustrated in Table 3, the process described herein was able to extract the high molecular weight naphthenic tetra-acids, particularly ARN acids, at a purity of 53 percent with an 18 percent yield on the deposits by weight.

TABLE 3

Calculated Compositions and Yields from Two Extraction Experiments

| | | Solid Calcium Naphthenate Deposits, Composition |
|---|---|---|
| Extraction balance | | |
| Solids | S | 24% |
| Organics (ARN + Entrained Oil) | (A + E) | 34% |
| Aqueous (Ca) (by difference) | C | 42% |
| Soxhlet balance | | |
| Entrained Oil | E | 16% |
| Soxhlet Solids | (S + C + A) | 84% |
| | | Yields |
| ARN yield | A = (A + E) − E | 18% |
| Extraction ARN purity | A/(A + E) | 53% |

While the disclosed subject matter has been described with reference to one or more particular embodiments, those skilled in the art will recognize that many changes can be made thereto without departing from the spirit and scope of the disclosed subject matter. Each of these embodiments and obvious variations thereof is contemplated as falling within the spirit and scope of the claimed disclosed subject matter, which is set forth in the following claims. The disclosed subject matter is therefore to be limited only by the terms of the appended claims along with the full scope of equivalents to which the claims are entitled.

What is claimed is:

1. A method for recovering naphthenic tetra-acids from a calcium naphthenate deposit, the method comprising:
    contacting a calcium naphthenate deposit comprising calcium naphthenate salts of naphthenic tetra-acids and entrained crude oil with
        an aqueous solvent solution comprising an aqueous acid and an organic solvent in a volumetric ratio-effective to dissociate the calcium naphthenate salts into naphthenic tetra-acids and calcium salts and to dissolve the naphthenic acids in the organic solvent and
    form a multiphase mixture;
    separating the multiphase mixture into a plurality of phases including an aqueous acid phase and an organic solvent phase containing the naphthenic tetra-acids;
    recovering the naphthenic tetra-acids from the organic solvent phase.

2. The method of claim 1, wherein the multiphase mixture is filtered to remove solids comprising at least one of inorganic salts, oxides, metals and any unreacted organic acid salts.

3. The method of claim 1, further comprising washing the aqueous acid phase with an effective amount of additional organic solvent to dissolve tetra-acids present in the acid phase into the additional organic solvent, separating the aqueous acid phase and the additional organic solvent phase, and combining the additional organic solvent phase with the organic solvent phase from the previous separation, prior to the recovery step.

4. The method of claim 1, further comprising drying the organic solvent phase using a chemical drying agent, prior to the recovery step.

5. The method of claim 1, wherein the naphthenic tetra-acids are recovered from the organic solvent phase by evaporation of the organic solvent.

6. The method of claim 1, wherein the aqueous acid is selected from the group consisting of hydrochloric, sulfuric, nitric, acetic, and phosphatic acid.

7. The method of claim 1, wherein the organic solvent is selected from the group consisting of alkyl halides, light aromatic hydrocarbons, and light hydrocarbon-light alcohol mixtures.

8. The method of claim 7, wherein the organic solvent is methylene chloride.

9. The method of claim 1, wherein the aqueous solvent solution comprises a volumetric ratio of 1:1 of the aqueous acid to the organic solvent.

10. The method of claim 1, wherein the effective mass ratio of aqueous solvent solution to calcium naphthenate deposit is 40:1.

11. The method of claim 1, wherein the separation step is achieved using gravity settling, electrostatic field separation, centrifugation or a combination thereof.

12. The method of claim 4, wherein the chemical drying agent is selected from the group consisting of anhydrous sodium sulfate, gypsum (calcium sulfate), calcium chloride, or silica gel.

13. The method of claim 1, wherein the naphthenic tetra-acids are ARN acids.

14. The method of claim 1, wherein the naphthenic tetra-acids have a molecular weight ranging from about 1228 to about 1236 atomic mass units (amu).

* * * * *